United States Patent
Inthasaro

(10) Patent No.: US 10,533,082 B2
(45) Date of Patent: Jan. 14, 2020

(54) NITRILE RUBBER GLOVE WITH STRETCH MODIFIER

(71) Applicant: O&M Halyard, Inc., Mechanicsville, VA (US)

(72) Inventor: Jumnong Inthasaro, Tambol Prik (TH)

(73) Assignee: O&M Halyard, Inc., Mechanicsville, VA (US)

( * ) Notice: Subject to any disclaimer, the term of this patent is extended or adjusted under 35 U.S.C. 154(b) by 89 days.

(21) Appl. No.: 15/564,988

(22) PCT Filed: Mar. 28, 2016

(86) PCT No.: PCT/US2016/024425
§ 371 (c)(1),
(2) Date: Oct. 6, 2017

(87) PCT Pub. No.: WO2016/175954
PCT Pub. Date: Nov. 3, 2016

(65) Prior Publication Data
US 2018/0312671 A1    Nov. 1, 2018

Related U.S. Application Data

(60) Provisional application No. 62/153,546, filed on Apr. 28, 2015.

(51) Int. Cl.
C08L 9/04     (2006.01)

(52) U.S. Cl.
CPC ........................... C08L 9/04 (2013.01)

(58) Field of Classification Search
CPC ................................................... C08L 9/04
See application file for complete search history.

(56) References Cited

U.S. PATENT DOCUMENTS

| | | | |
|---|---|---|---|
| 5,014,362 A * | 5/1991 | Tillotson | A41D 19/0055 2/167 |
| 6,031,042 A | 2/2000 | Lipinski | |
| 6,451,893 B1 | 9/2002 | Tao | |
| 6,566,435 B1 | 5/2003 | Teoh et al. | |
| 7,037,579 B2 | 5/2006 | Hassan et al. | |
| 8,117,672 B2 | 2/2012 | Lipinski | |
| 8,250,673 B2 | 8/2012 | Lipinski | |
| 8,758,662 B2 | 6/2014 | Lipinski | |
| 8,936,843 B2 | 1/2015 | Lipinski et al. | |
| 2005/0197480 A1 | 9/2005 | Temple et al. | |
| 2006/0253956 A1 * | 11/2006 | Lipinski | A41D 19/0055 2/168 |
| 2008/0263829 A1 | 10/2008 | Diasio | |
| 2013/0232663 A1 * | 9/2013 | Foo | A41D 19/0058 2/168 |

FOREIGN PATENT DOCUMENTS

| | | |
|---|---|---|
| EP | 1 143 817 B1 | 12/2009 |
| WO | WO 99/24507 | 5/1999 |
| WO | WO 01/90236 A1 | 11/2001 |

OTHER PUBLICATIONS

Handbook of Green Chemicals, Michael Ash, Synapse Info Resources, 2004; p. 339.*
Michem Lube 135 Technical Data Sheet, 2019 Michelman, Inc.*
International Search Report for PCT/US2016/024425, dated Nov. 17, 2016, 4 pages.

* cited by examiner

*Primary Examiner* — Michael F Pepitone
(74) *Attorney, Agent, or Firm* — Dority & Manning, P.A.

(57) ABSTRACT

An improved nitrile rubber formulation and process for making elastomeric nitrile rubber articles from the nitrile rubber formulation are disclosed. In particular, the nitrile rubber formulation can produce nitrile rubber based articles which exhibit force-strain characteristics that are comparable to those of natural rubber latex articles, while maintaining the tensile strength properties of nitrile rubber. The process includes adding a stretch modifier during the compounding of the nitrile rubber formulation. The invention also includes an elastomeric nitrile rubber product made by the process, such as examination glove, surgical glove, etc.

18 Claims, 2 Drawing Sheets

NITRILE RUBBER GLOVE WITH STRETCH MODIFIER

RELATED APPLICATION

The present application is the national stage entry of International Patent Application No. PCT/US2016/024425 having a filing date of Mar. 28, 2016, which claims priority to U.S. provisional application Ser. No. 62/153,546, filed on Apr. 28, 2015, both of which are incorporated herein in their entirety by reference thereto.

FIELD OF INVENTION

The present invention relates to elastomeric articles that are made from nitrile rubber formulations. In particular, the invention pertains to nitrile rubber articles that exhibit physical characteristics that are comparable to similar articles made from natural rubber latex.

BACKGROUND OF THE INVENTION

The development of modern rubber materials has made possible the manufacture of a wide range of elastomeric articles having varying properties of strength and chemical resistance. As synthetic latex materials have developed, various elastic and polymeric materials have been adapted for use in making a variety of articles of manufacture. One useful class of synthetic rubber material compounds includes the nitrile rubber class, which is widely used to make articles such as gloves and oil resistant seals.

Elastomeric articles requiring the highest elongation and greatest ease to stretch, such as surgical or examination gloves, balloons, and condoms have traditionally been made from natural rubber latex. While nitrile rubber products are typically more difficult to stretch, one of the advantages of nitrile rubber over natural rubber latex substrates is that nitrile rubber products do not contain natural latex proteins, which can become a significant allergy issue for some users. Other advantages of nitrile rubber materials over natural rubber latex are that nitrile rubber materials exhibit improved chemical resistance, especially to fatty and oily substances, and improved puncture resistance. Hence, nitrile rubber products have become desirable as a substitute for natural rubber products.

While hospitals, laboratories, or other work environments that may use rubber gloves often want to go "latex free" to better protect their workers, the normally higher cost of nitrile rubber products often limits their ability to make the change. Another hindrance toward making the change is that nitrile rubber gloves traditionally have been stiffer, hence such gloves are less comfortable to wear as compared to similar types of gloves made from natural rubber latex materials.

Currently, it is believed that no nitrile rubber examination gloves are available on the commercial market that exhibit stress-strain and force-strain properties that are close to that of natural rubber latex gloves, not to mention being either similar or the same as natural rubber latex gloves in these terms. Stress-strain properties measure the response to an applied force per unit cross sectional area of the material, while force-strain properties refer to a direct measurement of how a material responds (stretches) in response to an applied force, regardless of the thickness of the material. For instance, natural rubber latex (NRL) examination gloves typically only require a stress of about 4.5 MPa to stretch to an elongation of about 500% over original dimensions. This often is referred to as the glove's 500% modulus. Conventional nitrile rubber examination gloves, on the other hand, typically require more than twice that amount of stress (e.g., about 10 MPa) to achieve the same 500% elongation. In addition, NRL examination gloves typically only require a force of about 1.2 Newtons to stretch to an elongation of 400%. Meanwhile, conventional nitrile rubber examination gloves require a force of about 2.25 Newtons to stretch to an elongation of 400%.

Nitrile rubber, a synthetic polymer often used in emulsion (latex) form to manufacture medical and industrial gloves is a random terpolymer of acrylonitrile, butadiene, and a carboxylic acid such as methacrylic acid. It can be cross-linked by two separate mechanisms to improve its strength and chemical resistance. The first mechanism of crosslinking occurs by ionically bonding carboxylic acid groups together using multivalent metal ions. These ions are typically supplied through addition of zinc oxide to the emulsion. Normally the strength and stiffness/softness of the polymer is very sensitive to this type of crosslinking. The other crosslinking mechanism is a covalent crosslinking of the butadiene segments of the polymer using sulfur and catalysts known as rubber accelerators. This covalent crosslinking is especially important for development of chemical resistance. Gloves are often formed by first placing a coagulant solution, which can contain calcium nitrate, calcium carbonate, or a combination thereof, on ceramic glove molds, then dipping into the nitrile rubber to cause local gelation of the nitrile rubber over the mold surface.

Several prior approaches to softening nitrile rubber articles have involved strongly limiting or completely omitting zinc oxide and other materials capable of ionically crosslinking carboxylated nitrile rubber, such as those described in U.S. Pat. Nos. 6,031,042 and 6,451,893. In addition to not yielding force-strain properties similar to those of comparable natural rubber products as discussed above, this method can result in a material having lower strength, the need for higher curing temperatures, the need for extraordinarily high levels of other chemicals that may cause skin irritation, or processing difficulties such as thickening of the nitrile rubber before dipping.

Other approaches to making a nitrile glove more comfortable, such as those described in U.S. Pat. Nos. 5,014,362 and 6,566,435, have relied on stress relaxation over time and require constantly applied levels of strain to cause the desired relaxation or softening. Such determination measures are difficult to maintain and can be unrealistic in real world practice and use.

As such, a need exists for a nitrile rubber-based article that can successfully combine the benefits of nitrile rubber materials with the greater pliability or softness of natural rubber latex without the need to apply conditions required for softening caused by stress relaxation. There is also a need for a kind of nitrile glove that can incorporate a polymer formulation and product dimensions to simulate the comfort and softness associated with natural rubber latex products, while simultaneously maintaining the protective and non-allergenic properties of nitrile rubber. Desirably, such a glove, when worn, would enable the elastomeric material to exhibit physical strain or stress profiles similar to those of natural rubber, without exposure to natural rubber's associated problems.

SUMMARY OF THE INVENTION

The present invention pertains to an elastomeric, nitrile rubber article that exhibits improved force-strain characteristics as compared to conventional nitrile rubber articles and that exhibits force-strain characteristics that are comparable or similar to that of natural rubber latex (NRL) or polyisoprene articles, while preserving the tensile strength and protective properties of conventional nitrile rubber articles. In particular, the invention describes relatively thin elastic articles, such as a glove, that are thinner, softer, and more pliable conventional nitrile gloves, yet are designed still to retain the protective properties and maintain sufficient strength for industrial, clean room, or laboratory work and all medical procedures in which nitrile rubber gloves are normally worn. In other words, the nitrile rubber glove of the present invention exhibits force-strain response characteristics similar to or even improved as compared to NRL gloves and exhibits stress-strain response characteristics similar to that of NRL gloves.

In one embodiment, the present invention is directed to an elastomeric article that includes a compounded nitrile rubber formulation. The compounded nitrile rubber formulation includes a nitrile rubber, an alkali agent, a metal oxide, sulfur crosslinking agent, a vulcanization accelerator, and a stretch modifier.

In one particular embodiment, the nitrile rubber can be a carboxylated acrylonitrile butadiene rubber. In an additional embodiment, the alkali agent can include potassium hydroxide, ammonium hydroxide, or a combination thereof. In another embodiment, the alkali agent can be present in the compounded rubber nitrile formulation in an amount ranging from about 0.1 parts to about 0.99 parts based on 100 dry parts of the nitrile rubber. In still another embodiment, the metal oxide can include zinc oxide. Further, the metal oxide can be present in the compounded rubber nitrile formulation in an amount ranging from about 0.01 parts to about 0.5 parts based on 100 dry parts of the nitrile rubber. In addition, the combined amount of the alkali agent and the metal oxide present in the compounded rubber nitrile formulation can be less than or equal to 1, based on 100 dry parts of the nitrile rubber. In yet another embodiment, the sulfur crosslinking agent can be present in the compounded rubber nitrile formulation in an amount ranging from about 0.1 parts to about 5 parts, based on 100 dry parts of the nitrile rubber.

In still another embodiment, the vulcanization accelerator can include a dithiocarbamate, a thiazole, a guanidine, or a combination thereof. Additionally, the vulcanization accelerator can be present in the compounded rubber nitrile formulation in an amount ranging from about 0.1 parts to about 5 parts, based on 100 dry parts of the nitrile rubber.

In one more embodiment of the present invention, the stretch modifier can be a wax emulsion. For example, the wax emulsion can include a micronized wax. The micronized wax can have a mean particle size ranging from about 0.1 micrometers to about 50 micrometers. Further, the micronized wax can include a polyethylene wax, an oxidized polyethylene wax, a modified polyethylene wax, a high density polyethylene wax, an oxidized high density polyethylene wax, a modified high density polyethylene wax, a polypropylene wax, a polyamide wax, a polytetrafluoroethylene wax, or a combination thereof. Moreover, the stretch modifier can be present in the compounded rubber nitrile formulation in an amount ranging from about 0.1 parts to about 10 parts, based on 100 dry parts of the nitrile rubber.

In still another embodiment, the elastomeric article can include a nitrile rubber formulation that has a pH ranging from about 9 to about 11. Additionally, the compounded nitrile rubber formulation can, in some embodiments, have a total solids content ranging from about 28% to about 38%.

In one more embodiment of the present invention, a stress of about 8 MPa or less is required to stretch the elastomeric article to an elongation of about 500%.

Further, a force of about 2 Newtons or less can be required to stretch the elastomeric article to an elongation of about 400%. Moreover, the elastomeric article can exhibit a force at break ranging from about 8 Newtons to about 14 Newtons, wherein the elastomeric article has a thickness of about 0.05 mm to about 0.15 mm in the palm region. The elastomeric article can also a tensile strength at break ranging from about 20 MPa to about 50 MPa, wherein the elastomeric article has a thickness of about 0.05 mm to about 0.15 mm in the palm region. In a further embodiment, the elastomeric article can exhibit an elongation at break ranging from about 650% to about 800%. In an additional embodiment, the elastomeric article can exhibit an elastic modulus of ranging from about 2.8 MPa to about 5 MPa at 300% stretch-elongation.

Also contemplated by the present invention is a method of making an elastomeric article. The method includes: a) preparing a compounded nitrile rubber formulation comprising a nitrile rubber, an alkali agent, a metal oxide, sulfur crosslinking agent, a vulcanization accelerator, and a stretch modifier; b) dipping a mold into the compounded rubber nitrile formulation; and c) curing said compounded nitrile rubber formulation to form the elastomeric article.

In one particular embodiment, the nitrile rubber can be a carboxylated acrylonitrile butadiene rubber. Meanwhile, the alkali agent can include potassium hydroxide, ammonium hydroxide, or a combination thereof. Further, the alkali agent can be present in the compounded rubber nitrile formulation in an amount ranging from about 0.1 parts to about 0.99 parts based on 100 dry parts of the nitrile rubber. Moreover, the metal oxide can include zinc oxide and can be present in the compounded rubber nitrile formulation in an amount ranging from about 0.01 parts to about 0.5 parts based on 100 dry parts of the nitrile rubber. Additionally, the combined amount of the alkali agent and the metal oxide present in the compounded rubber nitrile formulation can be less than or equal to 1, based on 100 dry parts of the nitrile rubber. In still another embodiment, the sulfur crosslinking agent can be present in the compounded rubber nitrile formulation in an amount ranging from about 0.1 parts to about 5 parts, based on 100 dry parts of the nitrile rubber.

In yet another embodiment, the vulcanization accelerator can include a dithiocarbamate, a thiazole, a guanidine, or a combination thereof. In addition, the vulcanization accelerator can be present in the compounded rubber nitrile formulation in an amount ranging from about 0.1 parts to about 5 parts, based on 100 dry parts of the nitrile rubber.

In one more embodiment, the stretch modifier can be a wax emulsion. The wax emulsion can include a micronized wax. Additionally, the micronized wax can have a mean particle size ranging from about 0.1 micrometers to about 50 micrometers. Moreover, the micronized wax can include a polyethylene wax, an oxidized polyethylene wax, a modified polyethylene wax, a high density polyethylene wax, an oxidized high density polyethylene wax, a modified high density polyethylene wax, a polypropylene wax, a polyamide wax, a polytetrafluoroethylene wax, or a combination thereof.

Moreover, the stretch modifier can be present in the compounded rubber nitrile formulation in an amount ranging from about 0.1 parts to about 10 parts, based on 100 dry parts of the nitrile rubber.

In still another embodiment of the present invention, the nitrile rubber formulation can be adjusted to a pH ranging from about 9 to about 11. In addition, the compounded nitrile rubber formulation can have a total solids content ranging from about 28% to about 38%.

In one particular embodiment, a stress of about 8 MPa or less can be required to stretch the elastomeric article to an elongation of about 500%. In still another embodiment, a force of about 2 Newtons or less can be required to stretch the elastomeric article to an elongation of about 400%. Furthermore, the elastomeric article can exhibits a force at break ranging from about 8 Newtons to about 14 Newtons, wherein the elastomeric article has a thickness of about 0.05 mm to about 0.15 mm in the palm region. Moreover, the elastomeric article can exhibit a tensile strength at break ranging from about 20 MPa to about 50 MPa, wherein the elastomeric article has a thickness of about 0.05 mm to about 0.15 mm in the palm region. Additionally, the elastomeric article can exhibit an elongation at break ranging from about 650% to about 800%. Further, the elastomeric article can exhibits an elastic modulus of ranging from about 2.8 MPa to about 5 MPa at 300% stretch-elongation.

Additional features and advantageous of the present invention will be revealed in the following detailed description. Both the foregoing summary and the following detailed description and examples are merely representative of the invention, and are intended to provide an overview for understanding the invention as claimed.

BRIEF DESCRIPTION OF THE FIGURES

A full and enabling disclosure of the present invention to one skilled in the art, including the best mode thereof, is set forth more particularly in the remainder of the specification, including reference to the accompanying figures, in which.

DETAILED DESCRIPTION OF REPRESENTATIVE EMBODIMENTS

Figure 1:
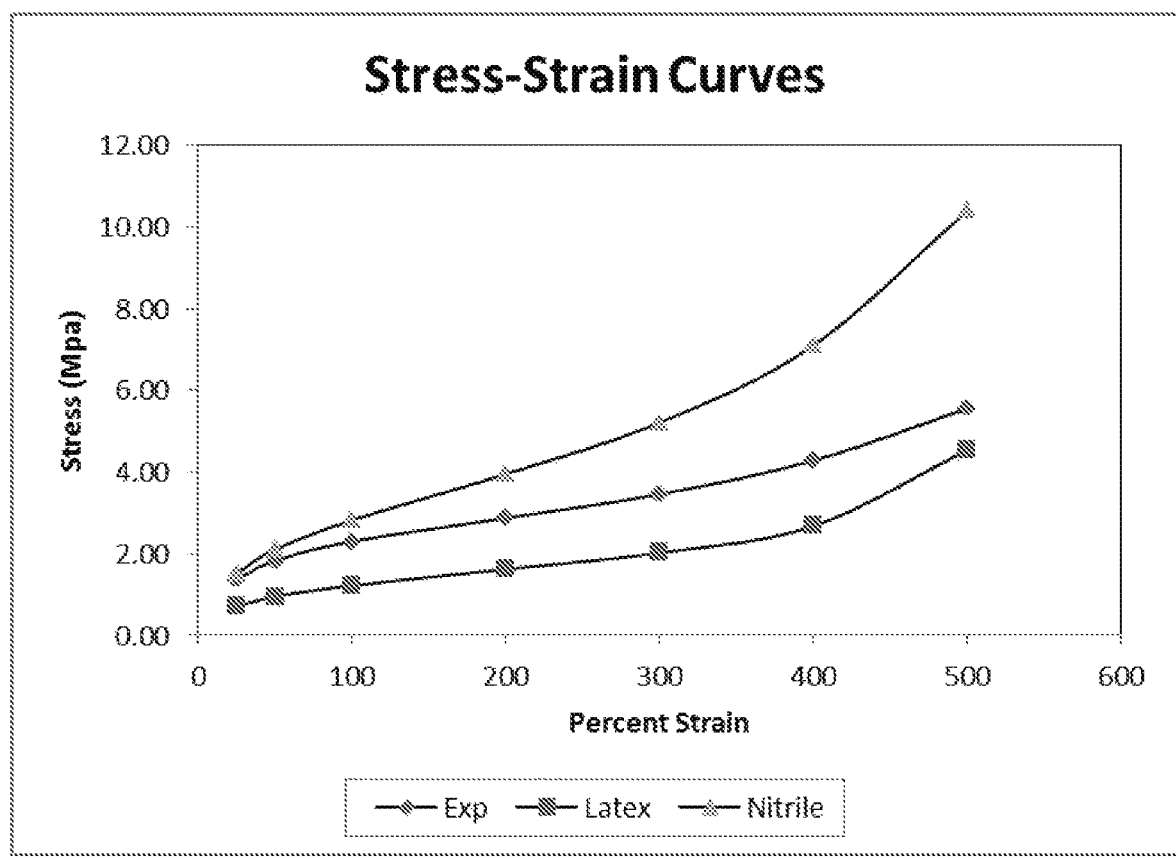
FIG. 1 is a graph showing three stress-strain curves, illustrating the difference in relative amount of stretch deformation caused by a wide range of stresses applied to samples from gloves made from a natural rubber latex, a conventional nitrile rubber formulation, and the nitrile rubber formulation of the present invention (Exp).

Generally speaking, the present invention describes the creation of elastomeric articles, such as gloves, made from a nitrile rubber formulation, and having physical characteristics similar to those of comparable natural rubber latex articles. A desirable attribute for elastomeric articles that are worn on the body is softness or pliability of the polymeric material. The invention describes the use of nitrile rubber formulations for manufacturing articles that have good physical strength and chemical resistance while also being softer (i.e., having a lower elastic modulus) than conventional nitrile rubber compositions. As used herein, the terms "elastic" or "elastomeric" generally refer to a material that, upon application of a force, is stretchable to an extended, biased length. Upon release of the stretching, biasing force, the material will substantially recover to near net shape or original dimensions; alternatively at least about 50% of the distorted or extended dimensions. As used herein, the term "stretch-elongation" refers to the amount or percentage that an elastomeric substrate or membrane is stretched or expanded exceeding its original dimensions. The "percent (%) deformation" or "percent (%) elongation" can be determined according to the following calculation: (Final Dimension−Initial Dimension)/Initial Dimension×100.

Traditionally, two methods have been used to create softer, more pliable elastomeric articles. One method is to make the substrate or membrane walls of the article thinner. The second method is to reduce the elastic modulus of the elastomeric material. Each of these two approaches has associated benefits and disadvantages. For instance, in both gloves and condoms, a thinner polymer membrane tends to enable the user to experience greater tactile sensitivity. Also, often the thinner the elastic synthetic polymer walls become, the less amount of force is needed to flex, stretch, or deform the article. Thinness, however, can often be associated with problems such as weak tensile strength or a tendency of the article to rupture under use. Decreasing the elastic or Young's modulus, on the other hand, allows one to retain a relatively thicker substrate and still impart ease of flexibility when a glove is worn on the hand. However, decreasing the modulus of a rubber formulation by reducing the level of crosslinking in the polymer often also results in lower strength or lower chemical resistance.

The force response behavior of conventional nitrile rubber gloves is normally very different from that of similar natural rubber latex gloves. When similar forces are applied to both kinds of materials, the amount of instantaneous stretch would be much higher for the natural rubber glove when compared to a conventional nitrile rubber glove. While this difference in the amount of stretch can be reduced through various approaches, such as by reducing or even eliminating the amount of metal oxide crosslinking, reduction of the level of metal oxides to an extremely low level required to close the relatively large gap in difference between the two kinds of polymers often can irrevocably compromise the strength of the article or can adversely affect the dipping process used during manufacturing (i.e., slower gelation, slower covalent crosslinking, viscosity increase, etc.), while still not simulating the lower degree of force response associated with natural rubber latex very closely.

As such, the present inventors have discovered that an elastomeric glove formulation including a specific combination of components in specific amounts can result in a nitrile rubber glove that is comparable to natural rubber latex gloves in terms of softness and stretchability, yet without sacrificing the strength and protective properties that can be provided by conventional nitrile rubber gloves.

The gloves made using the nitrile rubber formulation of the present invention are softer and more pliable to wear than conventional nitrile rubber gloves, hence providing greater comfort compared to the wearer. Further, the gloves of the present invention can provide a wearer with greater tactile sensation in the hand and finger tips than compared with regular gloves. The softness and pliability can be controlled by varying the specific components of the nitrile rubber formulation. Moreover, such advantages can be realized with no compromise in the strength of the glove.

Generally, a glove made according to the present invention can have a palm thickness in a range between about 0.05 mm and about 0.15 mm, a cuff thickness between about 0.03 mm and about 0.13 mm, and a finger thickness between about 0.07 mm and about 0.17 mm. Further, a glove made according to the present invention only requires a stress of about 8 MPa or less, such as from about 1 MPa to about 7 MPa, such as from about 1.5 MPa to about 6 MPa, such as from about 2 MPa to about 5.5 MPa to stretch to an elongation of about 500%. In stark contrast and referring to FIG. 1, convention nitrile rubber gloves require a stress of at least about 10 MPa to stretch to an elongation of about 500%. Meanwhile, natural rubber latex gloves require a stress of about 4.5 MPa to stretch to an elongation of about 500%. Moreover, a glove made according to the present invention only requires a force of about 2 Newtons (N) or less, such as from about 0.1 N to about 1.75 N, such as from about 0.25 N to about 1.5 N, such as from about 0.5 N to about 1.1 N to stretch to an elongation of about 400%. In stark contrast and referring to FIG. 2, conventional nitrile rubber gloves require a force of at least about 2.25 N to stretch to an elongation of about 400%. Meanwhile, natural rubber latex gloves require a force of about 1.17 N to stretch to an elongation of about 400%. Thus, the gloves contemplated by the present invention require less force than both natural rubber latex and conventional nitrile gloves to stretch to an elongation of about 400% and require a comparable level of stress as natural rubber latex gloves to stretch to an elongation of about 500% and a much lower stress than that required for conventional nitrile gloves to stretch to an elongation of about 500%.

In addition, a glove formed from the nitrile rubber formulation of the present invention with a thickness of about 0.13 mm in the palm area has a force-at-break ranging from about 8 Newtons (N) to about 14 N, such as from about 8.5 N to about 13 N, such as from about 9 N to about 12 N. Further, a glove formed from the nitrile rubber formation of the present invention has a tensile strength at break that ranges from about 20 MPa to about 50 MPa, such as from about 25 MPa to about 40 MPa, such as from about 28 MPa to about 35 MPa. Moreover, a glove formed from the nitrile rubber formulation of the present invention has an elongation at break ranging from about 650% to about 800%, such as from about 675% to about 775%, such as from about 690% to about 750%. Additionally, at about 300% stretch-elongation, the modulus of a glove formed from the nitrile rubber formulation of the present invention ranges from about 2.8 MPa to about 5 MPa, such as from about 2.9 MPa to about 4.5 MPa, such as from about 3 MPa to about 4 MPa.

The precise point of measurement in order to determine that data described above is that defined in American Society for Testing and Materials (ASTM) test standard D-412-98a (Reapproved 2002), "Standard Test Methods for Vulcanized Rubber and Thermoplastic Elastomers—Tension, published January 2003, the contents of which are incorporated herein by reference. These test methods cover procedures used to evaluate the tensile (tension) properties of vulcanized thermoset rubbers and thermoplastic elastomers. The determination of tensile properties starts with test pieces taken from a sample material and includes the preparation of specimens and the testing of the specimens. Specimens may be in the shape of dumbbells, rings, or straight pieces of uniform cross-sectional area. Measurements of tensile stress, tensile stress at a given elongation, tensile strength, yield point, and ultimate elongation are made on specimens that have not been pre-stressed. Tensile stress, tensile strength, and yield point are based on the original cross-sectional area of a uniform cross-section of the specimen.

The nitrile rubber formulation, glove formation procedures, and several examples contemplated by the present invention are discussed in more detail below.

I. Nitrile Rubber Formulation

The nitrile rubber formulation of the present invention, which can be used to form a glove having the aforementioned properties, can include a carboxylated nitrile that is compounded with various components based on 100 parts of the carboxylated nitrile. The carboxylated nitrile rubber and the various components compounded with the nitrile rubber in the formulation of the present invention are discussed in more detail below.

A. Carboxylated Nitrile Rubber

Carboxylated nitrile, which is a terpolymer of butadiene, acrylonitrile, and organic acid monomers, has at least two properties that make it useful for manufacturing elastomeric articles. These two features are high strength and impermeability to certain hydrocarbon solvents and oils. Compounding and curing the rubber (which is used in latex form for dipping to provide articles of manufacture such as gloves or condoms) with other ingredients such as curing agents, accelerators, and activators is generally performed to optimize these properties. The level of each monomer in the polymer and the level of curing can affect the levels of strength and the chemical resistance in the finished article. Polymers with higher levels of acrylonitrile tend to have better resistance to aliphatic oils and solvents, but are also stiffer than polymers that have lower levels of acrylonitrile. While the chemical nature of the monomers from which the polymer is made offers some degree of chemical resistance, when the polymer molecules are chemically crosslinked, resistance to chemical swelling, permeation, and dissolution greatly increase.

The base polymer employed in the present nitrile material can be a random terpolymer composition containing acrylonitrile, butadiene, and carboxylic acid components. It is believed that the particular advantageous properties of the present soft nitrile rubber materials can be due in part to the nature and interaction of a blend of acrylonitrile components in the composition. The blend can include two—a first and a second—acrylo-nitrile formulations in a compositional ratio ranging, respectively, from about 60:40 to 40:60. The orientation or placement of carboxyl groups on the nitrile polymer molecules—either outside or inside—can affect the reactivity of the carboxyl groups with zinc ions; hence, it is believed that some components exhibit softer, lower modulus properties and some components have good film forming properties.

The acrylonitrile content of the blended or combined terpolymer composition can range from about 17% by weight to about 45% by weight, such as from about 20% by weight to about 40% by weight, such as from about 20% by weight to about 35% by weight. In one embodiment, for instance, the acrylonitrile content can be between about 22% by weight and about 28% by weight, the methacrylic acid content can be less than about 10% by weight, and the remainder of the polymer can be butadiene. The methacrylic acid content should be less than about 15% by weight, preferably about 10% by weight, with butadiene making up the remainder balance of the polymer. The base terpolymer is made through a process of emulsion polymerization, and can be used while still in emulsion form to manufacture gloves or other elastomeric articles.

Further, the acrylonitrile polymer formulations that may be employed in the present invention can have a glass transition temperature ($T_g$) ranging from about −30° C. to about −10° C., such as from about −28° C. to about −12° C. In some embodiments, desirable nitrile polymer formulations, such as PolymerLatex X-1133 or Synthomer 6311 available from PolymerLatex GmbH, and Synthomer Ltd., respectively, can have a $T_g$ between about −26° C. and about −18° C. Other nitrile formulations, such as Nantex 635t, commercially available from Nantex Industry Co., Ltd. (Taiwan, R.O.C.), can have a $T_g$ between about −25.5° C.

and about −23.4° C. Another suitable nitrile polymer contemplated for use in the elastomeric articles of the present invention is Lutex 111 manufactured by LG Chem, which has a $T_g$ ranging from about −22° C. to about −14° C. and a total solids content of about 44.5% to about 45.5% and a pH of from about 8.2 to about 8.8.

It is believed, however, that the nitrile butadiene polymer properties do not come from components of the nitrile material, but from the structure of the polymer, which in turn, is determined by polymerization conditions. Polymer properties are very much affected by the polymer structure. Molecular structure of polymers can be very complex, with variability in molecular weight, molecular weight distribution, amount of branching, amount of crosslinking during polymerization, many possible types of chemical addition for diene monomers, etc. When several monomer types are combined into a polymer such as in a carboxylated acrylonitrile butadiene polymer used for glove manufacture, the structure becomes even more complex. Overall levels of each monomer type and the sequencing of the monomer units also contribute to the properties of the resulting polymer. When the repeating structure of the monomer units is random, such as in the nitrile rubber used for gloves, the physical properties of the polymer have increased influence from the polymer linearity (vs. branching) and molecular weight as compared to the properties of a homopolymer. This is because the properties expected from a regular repeating structure of a polymer made only from each single monomer change once that repeating structure is interrupted or otherwise altered by the addition of other types of monomer units. A high level of any particular monomer will likely increase the chance of contributing properties expected from a homopolymer made from that monomer, due to increased similarity of the repeating structures.

In carboxylated nitrile rubber used for thin glove manufacture, the acrylonitrile and carboxylic acid, which typically total approximately 35% by weight, add some plastic like character to the polymer with respect to resilience, permanent set, and stress relaxation. They also prevent a regular cis-1,4 repeating structure that would give polybutadiene its highest resilience and lowest set/relaxation.

A general description of such a carboxylated nitrile rubber would be a long-chain random arrangement of its three component monomers, with branching and crosslinking. These branched, random terpolymers are former into discrete tiny particles that are emulsified in water. In addition to the polymer structure, the particle structure also plays a part in the final properties of a glove. Parameters such as particle size, particle size distribution, level of particle agglomeration, particle density, etc., affect how the product is formed, and also its eventual properties.

In the present invention, the polymer structure includes a random terpolymer (as opposed to block or alternating terpolymer) of acrylonitrile, butadiene, and carboxylic acid. The properties depend on the average molecular weight, the molecular weight distribution, the linearity or degree of branching, the gel content (crosslinking during polymerization), and the microstructure (which monomer units are next to each other in short sections of the polymer chain).

Regardless of the particular structure of the nitrile rubber used in the present invention, various additional components can be incorporated during the compounding of the nitrile rubber formulation to obtain an article having the desired properties.

B. Alkali Agent

An alkali agent can be added to the nitrile rubber formulation to adjust the pH of the nitrile rubber formulation. Any suitable alkali agent can be used, and, in some embodiments, the alkali agent can be potassium hydroxide, ammonium hydroxide, or a combination thereof. In any event, the alkali agent can be used to adjust the nitrile rubber formulation to a pH that can range from about 9 to about 11, such as from about 9.2 to about 10.5, such as from about 9.5 to about 10.2. In addition to acting as a pH adjuster, the alkali agent can be utilized in combination with a metal oxide as discussed below to facilitate the formation of a nitrile rubber formulation that has high strength. Specifically, the alkali agent can include monovalent ions, such as K, Na, or H, which, although they do not have sufficient electron capacity to accommodate a bond with a second methylacrylic acid unit, may allow for weaker forms of associative bonding. As such, the alkali agents (e.g., monovalent salts) that can be used to increase the pH of the nitrile rubber formulation may also swell the nitrile rubber particles, making more carboxylic acid groups accessible to other crosslinking agents, such as the metal oxides discussed in more detail below. The positive charge of the cation can well balance the negative electrons of the acidic carboxyl groups.

Regardless of the particular alkali agent utilized, the alkali agent can be present in the compounded nitrile rubber formulation in an amount ranging from about 0.1 parts to about 0.99 parts, such as from about 0.2 parts to about 0.95 parts, such as from about 0.3 parts to about 0.9 parts, based on 100 dry parts of the nitrile rubber.

C. Metal Oxide

An article formed from the nitrile rubber formulation of the present invention can include a rubber membrane that is more stretchable; hence, it has been found that persons who normally need to wear a large-size glove can use a medium-size version of a glove made from the present nitrile-based composition, without binding or loss of flexible comfort. Moreover, a thinner rubber membrane enhances tactile sensitivity to temperature and surface textures. These changes, however, often compromise strength, chemical resistance, or both, resulting in articles that are unsuitable for many applications. Accordingly, a soft nitrile rubber formulation having strength and chemical resistance similar to stiffer rubbers is highly desirable, where crosslinking agents may be utilized to enhance the elasticity, strength, and chemical resistance of nitrile rubber formulation.

The carboxylated nitrile rubber of the present invention can be chemically crosslinked in at least two ways: the butadiene subunits can be covalently crosslinked with sulfur and accelerators, while the carboxylated (organic acid) sites can be ionically crosslinked with metal oxides or salts. Ionic crosslinks, resulting from, for example, the addition of a metal oxide, such as zinc oxide, to the nitrile rubber formulation, can result in a nitrile rubber formulation having high tensile strength, puncture resistance, and abrasion resistance, as well as high elastic modulus (a measure of the force required to stretch a film of the rubber), but poor oil and chemical resistance, which is why a sulfur crosslinking agent can be added to the nitrile rubber formulation, as discussed in more detail below.

While some have described ways to make softer nitrile gloves without a metal oxide or via other means, the present invention provides a formulation that includes a metal oxide such as zinc oxide, which improves the dipping qualities and cure rates, although it is to be understood that the metal oxide is present in the formulation of the present invention in decreased amounts compared to conventional nitrile rubber formulations that include a metal oxide. In contrast, when zinc oxide is not employed, the curing time required to reach an optimum state of cure can be much longer and the curing may be less efficient. This means that the crosslinks are longer (more sulfur atoms per crosslink) and there may be a higher amount of sulfur that does not crosslink polymer chains. The result can be a less-effectively cured rubber that has lowered heat resistance and less chemical resistance.

While not intending to be bound by theory, it is believed that the matrix structure and strength of the nitrile rubber formulation of the present invention may result from the interaction of all ions present in the system, in particular, divalent or higher valence cations, with the carboxylic acid components of the polymer matrix. Divalent or multivalent cations, such as Mg, Ca, Zn, Cu, Ti, Cd, Al, Fe, Co, Cr, Mn, and Pb, can crosslink with the carboxyl groups of the ionized carboxylic acids, forming relatively stable bonds. Of these cation species, Mg, Ca, Zn, Cu, or Cd are more desirable. Preferably, the methylacrylic acid monomers are located relatively close to each other in the polymer matrix structure; in such a fashion, the divalent or multivalent cation can crosslink with two or more nearby acid units. The positive charge of the cation can well balance the negative electrons of the acidic carboxyl groups. It is believed that, absent divalent or multivalent cations, multiple polymer chains in the nitrile emulsions are not well crosslinked together.

Regardless of the particular metal oxide utilized, the metal oxide can be present in the compounded nitrile rubber formulation in an amount ranging from about 0.01 parts to about 0.5 parts, such as from about 0.05 parts to about 0.4 parts, such as from about 0.08 parts to about 0.3 parts, based on 100 dry parts of the nitrile rubber.

In an event, to facilitate the formation of a product having a combination of strength, pliability, and softness characteristics that are comparable to natural rubber latex gloves, the total combined amount of the alkali agent and metal oxide in the nitrile rubber formulation can be less than or equal to 1 part, based on 100 dry parts of the nitrile rubber.

D. Sulfur Crosslinking Agent

As mentioned above, a sulfur crosslinking agent can also be used in the nitrile rubber formulation to provide oil and chemical resistance to a finished product containing the formulation. Such crosslinking can provide resistance to chemical swelling, permeation, and dissolution. In contrast to the alkali agent and metal oxide crosslinking agents discussed above, the sulfur is used to covalently crosslink the butadiene subunits of the carboxylated nitrile rubber.

Sulfur can be present in the compounded nitrile rubber formulation in an amount ranging from about 0.1 parts to about 5 parts, such as from about 0.2 parts to about 2.5 parts, such as from about 0.5 parts to about 2 parts, based on 100 dry parts of the nitrile rubber.

E. Vulcanization Accelerator

A vulcanization accelerator can be used in combination with the sulfur crosslinking agent to provide the desired level of chemical resistance to the finished product. As with the sulfur crosslinking agent, the vulcanization accelerator can be used to covalently crosslink the butadiene subunits of the carboxylated nitrile rubber. The vulcanization accelerator can be a single dithiocarbamate accelerator that is added with sulfur. However, in other cases where higher levels of chemical resistance are needed, a combination of vulcanization accelerators can be utilized. Such a combination can include a dithiocarbamate, a thiazole, and a guanidine compound, which can be present according to a ratio of about 1:1:2. For example, the vulcanization accelerator can be zincediethyldithiocarbamate (ZDEC), zinc mercaptobenzothiazole (ZMBT), diphenyl guanidine (DPG), or a combination thereof.

Regardless of the particular vulcanization accelerator or combination of vulcanization accelerators utilized, the vulcanization accelerator can be present in the compounded nitrile rubber formulation in an amount ranging from about 0.1 parts to about 5 parts, such as from about 0.2 parts to about 2.5 parts, such as from about 0.5 parts to about 2 parts, based on 100 dry parts of the nitrile rubber. In one particular embodiment, the compounds are zincdiethyldithiocarbamate (ZDEC), zinc mercaptobenzothiazole (ZMBT), and diphenyl guanidine (DPG), at about 0.25 parts ZMBT, 0.25 parts ZDEC, and 0.5 parts DPG, based on 100 dry parts of nitrile rubber.

F. Stretch Modifier

As mentioned above, the nitrile rubber formulation of the present invention uses ionic crosslinking via a metal oxide. Ionic crosslinking, however, often increases the stiffness of an article made from the rubber. This is a disadvantage for applications in which a softer rubber is needed. For example, surgical gloves made of soft rubbers can provide greater tactile sensitivity for the wearer, which is desirable to improve the surgeon's "feel" during operations and to prevent fatigue of the hands. As such, in order to improve the slip and softness of article formed from the nitrile rubber formulation of the present invention without compromising the strength and elasticity provided the crosslinking agents discussed above, the nitrile rubber formulation of the present invention includes a stretch modifier that is added directly into the formulation during compounding. Generally speaking, this stretch modifier may be a wax emulsion that is blended into the formulation in the amounts or proportions identified herein. Unlike previous uses of wax emulsions to coat articles such as gloves, the present invention utilizes the wax emulsion blended or compounded directly into the nitrile rubber formulation in sufficient amounts to alter the stretch characteristics of the articles formed from the nitrile rubber formulation in comparison to identical formulations that do not include the stretch modifiers. Another characteristic of the stretch modifier is that it is relatively inert and does significantly interfere with or alter the crosslinking of the nitrile rubber formulation.

In one particular embodiment, any suitable wax emulsion can be utilized in the nitrile rubber formulation of the present invention. In one particular embodiment, the wax emulsion can be water soluble wax. The wax can be in powder form so that it can be easily compounded with the other components of the nitrile rubber formulation. To further facilitate the incorporation of the wax emulsion into the nitrile rubber formulation, the wax emulsion can be a micronized wax. Such waxes can provide excellent slip and a smooth feel to articles formed from the nitrile rubber formulation of the present invention, and can also provide enhanced abrasion resistance.

In another embodiment, the wax emulsion can be relatively inert, such that it exhibits little to no cross-linking. Specifically, the incorporation of a wax emulsion that is generally chemically non-reactive or inert prevents the wax emulsion from interfering with the other components of the nitrile rubber formulation. As such, the synergistic effects of the other components of the nitrile rubber formulation are not impacted by the incorporation of an inert wax emulsion, resulting in an elastomeric article having the desired chemical resistance and strength as well as the improved slip and smooth feel provided by the inert wax emulsion.

Suitable micronized waxes contemplated by the present invention include micronized waxes having a mean particle size ranging from about 0.1 micrometers to about 50 micrometers, such as from about 0.5 micrometers to about 25 micrometers, such as from about 1 micrometer to about 20 micrometers. Further, the micronized wax of the present invention can have a melting point ranging from about 90° C. to about 145° C., such as from about 95° C. to about 140° C., such as from about 100° C. to about 135° C. Specific examples of micronized wax contemplated by the present invention include polyethylene wax, oxidized polyethylene wax, modified polyethylene wax, high density polyethylene wax, oxidized high density polyethylene wax, modified high density polyethylene wax, polypropylene wax, polyamide wax, polytetrafluoroethylene wax, or a combination thereof. Particular examples of micronized waxes that can be used as the wax emulsion in the nitrile rubber formulation of the present invention include AQUA SUPERSLIP 6550, AQUA SYNFLUO 176, AQUAFLEX 212G, AQUAPOLY 215, AQUAPOLY 225, AQUAPOLY 250, AQUAPOLYFLUO 411, AQUAPOLYSILK 19, and AQUAWAX 114, all available from Micro Powders Inc. (Tarrytown, N.Y.).

Regardless of the particular stretch modifier utilized, the stretch modifier can be present in the compounded nitrile rubber formulation in an amount ranging from about 0.1 parts to about 10 parts, such as from about 0.2 parts to 8 parts, such as from about 0.4 parts to about 6 parts, based on 100 dry parts of the nitrile rubber.

G. Other Components

Although not required, the nitrile rubber formulation of the present invention can include titanium dioxide, a color pigment, or a combination thereof to provide a desired level of whiteness or opaqueness. If utilized, the titanium dioxide can be present in the compounded nitrile rubber formulation in an amount ranging from about 0.1 parts to about 5 parts, such as from about 0.2 parts to 4 parts, such as from about 0.4 parts to about 3 parts, based on 100 dry parts of the nitrile rubber. Meanwhile, if utilized, the color pigment present in the compounded nitrile rubber formulation in an amount ranging from about 0.1 parts to about 1 part, such as from about 0.2 parts to 0.9 parts, such as from about 0.3 parts to about 8 parts, based on 100 dry parts of the nitrile rubber.

Regardless of the specific components utilized to form the nitrile rubber formulation of the present invention, after compounding, the resulting nitrile rubber formulation can have a total solids content (TSC) a TSC of from about 28% to about 38%, such as from about 30% to about 36%, such as from about 31% to about 35%. The reduction of the TSC compared to the carboxylated nitrile rubber, which has a TSC of from about 44.5% to 45.5%, enables for the manufacture of articles that have a reduced thickness compared to some other nitrile rubber formulations.

The components of the nitrile rubber formulation can be compounded by adding them to the formulation in any order. However, in one particular embodiment, the alkali agent is added to the carboxylated nitrile rubber first, followed by the metal oxide, the vulcanization accelerator, the sulfur, and then the wax emulsion.

After the nitrile rubber formulation is compounded, the formulation can be used to form any suitable elastomeric article. In one particular embodiment, the nitrile rubber formulation can be used to form a substrate that is a glove, as discussed in more detail below.

II. Glove Formation

After the nitrile rubber formulation is compounded, it can be used in a coagulant dip-coating process to form an elastomeric glove. The process for forming an elastomeric glove entails providing a clean glove form or mold that is preheated to approximately 55-60° C., and preferably about 58° C. The prepared mold is then dipped into an aqueous solution of a coagulant (e.g., calcium nitrate, calcium carbonate, or a combination thereof). The mold, with coagulant on its surface, is dried and reheated to approximately 70° C.±5° C., and dipped into a bath of the compounded nitrile rubber formulation, forming a gelled glove. The mold with the gelled glove substrate applied thereon is then soaked in water to remove all of the water-soluble material components. The mold with the gelled glove substrate applied thereon is then dried in an oven at a temperature ranging from about 80° C. to about 100° C. When the mold with the gelled glove substrate applied thereon is then heated to a higher temperature, the sulfur reacts with the other components and crosslinks the methylacrylic acid units in the carboxylated nitrile rubber. Afterwards, the glove is removed from the mold, and the glove surfaces are treated with chlorinated water to reduce the tackiness of the glove surfaces. Finally, the resulting gloves are dried and readied for packaging.

During this process, faster entry and exit speeds of the glove mold into the nitrile rubber formulation dipping solution can provide a more even thickness profile to the glove, due at least in part to the reduced difference in residence time of the fingertip and cuff areas of the molds in the compounded nitrile rubber formulation. The mold can be extracted from the dip bath at or near an initial vertical position and raised such that the finger tips are elevated to a horizontal or greater than horizontal position (e.g., tilted to an angle of about 20° to 45° above horizontal) for a brief period of time ranging from a few seconds to about 40 seconds. Quickly thereafter, the finger tips can be lowered to a position or angle between horizontal and initial vertical, while rolling the mold along its longitudinal axis. The raising and lowering action can be repeated in a sinusoidal or wave-like motion. This process can enable the nitrile rubber formulation to distribute more evenly over the mold or former and produce a substrate product that is thinner overall.

The present invention may be better understood with reference to the following examples.

III. Examples

In the following examples, elastomeric gloves were made using the nitrile rubber formulation and coagulant dip-coating process described above and then subjected to mechanical testing. The nitrile rubber formulation included the components listed in Table 1 below.

TABLE 1

| Component | Parts Per 100 Parts of Nitrile Rubber |
|---|---|
| Nitrile Rubber | 100 |
| Potassium Hydroxide | 0.8 |
| Zinc Oxide | 0.2 |
| ZMBT | 1 |

TABLE 1-continued

| Component | Parts Per 100 Parts of Nitrile Rubber |
|---|---|
| Sulfur | 1 |
| Wax Emulsion | 4 |

The nitrile rubber formulation above had a pH of 9.47 and a total solids content (TSC) of 32.74%. Meanwhile, the finished glove had a TSC of 100% since the substrate should not contain appreciable or significant amounts of water.

The tensile testing parameters and methods for the examples below are defined in American Society for Testing and Materials (ASTM) test standard D-412-98a. In the present invention, the ASTM protocol was employed with no changes. The testing apparatus used was an Instron® tensometer, model 5564, with a static load cell of capacity about +/−100N, and a XL extensometer. However, it is to be understood that other similar kinds of equipment could be used, as long as the machine met the requirements of the ASTM standard.

Example 1

In Example 1, a glove sample made from the nitrile rubber formulation discussed above was subjected to mechanical testing where an increasing level of stress was applied until the glove sample exhibited an elongation of about 500%, and the stress was recorded. The results were then compared to a natural rubber latex (NRL) glove and a conventional rubber nitrile glove (e.g., a glove without the wax emulsion of the nitrile rubber formulation of the present invention).

As shown in FIG. 1, a glove made according to the present invention, labeled as "Exp," only required a stress of about 5 MPa to stretch to an elongation of about 500%. In stark contrast, a conventional nitrile rubber glove, labeled as "Nitrile," required a stress of at about 10 MPa to stretch to an elongation of about 500%. Meanwhile, a natural rubber latex glove, labeled as "Latex," required a stress of about 4.5 MPa to stretch to an elongation of about 500%. Thus, despite being formed from the nitrile rubber formulation of the present invention, the "Exp" glove of Example 1 demonstrated stretch deformation properties that were comparable to the natural rubber latex glove, while more than twice the amount of stress was required to be applied to the conventional nitrile rubber to reach the same 500% elongation.

Figure 2:
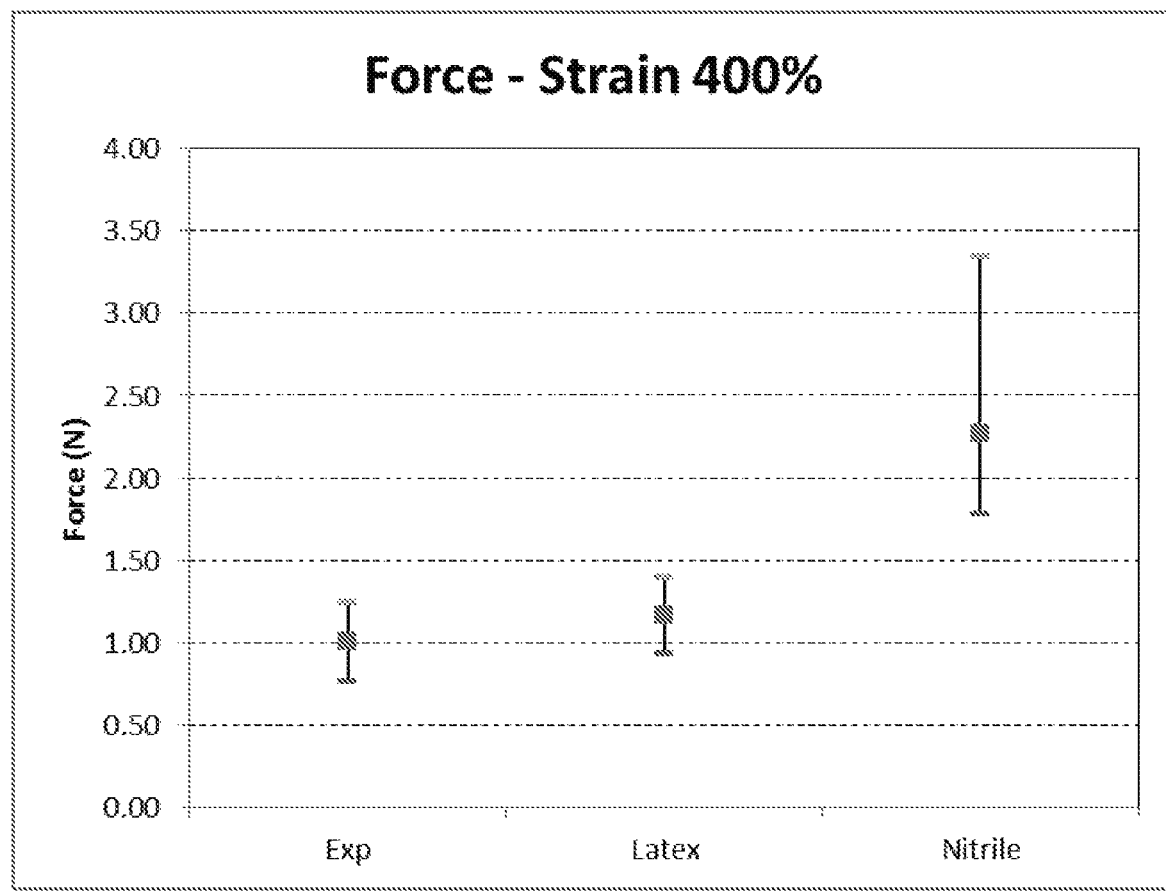
FIG. 2 is a graph showing the force-strain relationship for the same samples showing the force required to stretch the glove to an elongation of 400%.

Moreover, as shown in FIG. 2, a glove made according to the present invention, labeled as "Exp," only required a force of about 1 Newton (N) to stretch to an elongation of 400%. In stark contrast, a conventional nitrile rubber glove, labeled as "Nitrile," required a force of 2.27 N to stretch to an elongation of 400%. Meanwhile, a natural rubber latex glove, labeled as "Latex," required a force of 1.17 N to stretch to an elongation of 400%. Thus, the gloves contemplated by the present invention require less force than both natural rubber latex and conventional nitrile gloves to stretch to an elongation of about 400%.

In summary, the graphs shown in FIGS. 1 and 2 demonstrate that the products formed from the nitrile rubber formulation of the present invention differ from conventional nitrile rubber products with reference to the stress and force readings, where the stress readings are comparable to natural rubber latex gloves and the force readings are lower than that of natural rubber latex gloves. This phenomenon is believed to result from the specific combination and amounts of the components incorporated into the compounded nitrile rubber formulation of the present invention.

Example 2

Next, in Example 2, the nitrile rubber formulation of the present invention was used to make samples of gloves in sizes 7, 8, and 9. The dimensions for the various sizes are shown below in Table 2.

TABLE 2

| Glove Dimensions | | | |
|---|---|---|---|
| | Size 7 | Size 8 | Size 9 |
| Length (mm) | 310 | 310 | 310 |
| Palm Width (mm) | 98 | 113 | 124 |
| Cuff Thickness (mm) | 0.1 | 0.1 | 0.1 |
| Palm Thickness (mm) | 0.13 | 0.13 | 0.13 |
| Finger Thickness (mm) | 0.15 | 0.15 | 0.16 |

The modulus (MPa) at 25% elongation, 50% elongation, 100% elongation, 200% elongation, 300% elongation, 400% elongation, and 500% elongation was recorded for both unaged and aged glove samples. Further, the tensile strength at break (MPa), force at 300% elongation (N), force at 400% elongation (N), force at break (N), and elongation at break (%) were recorded for both unaged and aged glove samples. The testing results for unaged samples are summarized below in Table 3, while the testing results for aged samples are summarized below in Table 4, where the samples in Table 4 were aged at 70° C. for 168 hours.

TABLE 3

| Unaged Physical Properties | | | |
|---|---|---|---|
| Modulus (MPa) | Size 7 | Size 8 | Size 9 |
| 25% Elongation | 1.29 | 1.51 | 1.50 |
| 50% Elongation | 1.67 | 1.83 | 1.85 |
| 100% Elongation | 2.07 | 2.22 | 2.18 |
| 200% Elongation | 2.55 | 2.65 | 2.65 |
| 300% Elongation | 3.08 | 3.16 | 3.18 |
| 400% Elongation | 3.95 | 3.99 | 3.99 |
| 500% Elongation | 5.46 | 5.56 | 5.51 |
| Tensile Strength at Break (MPa) | 28.32 | 30.63 | 30.44 |
| Force at 300% Elongation (N) | 1.01 | 1.01 | 1.03 |
| Force at 400% Elongation (N) | 1.90 | 1.28 | 1.30 |
| Force at Break (N) | 9.23 | 9.83 | 9.90 |
| Elongation at Break (%) | 715 | 722 | 724 |

TABLE 4

| Aged Physical Properties | | | |
|---|---|---|---|
| Modulus (MPa) | Size 7 | Size 8 | Size 9 |
| 25% Elongation | 1.34 | 1.42 | 1.45 |
| 50% Elongation | 1.79 | 1.91 | 1.90 |
| 100% Elongation | 2.33 | 2.42 | 2.41 |
| 200% Elongation | 2.98 | 3.10 | 3.01 |
| 300% Elongation | 3.75 | 3.81 | 3.69 |
| 400% Elongation | 4.85 | 4.82 | 4.66 |
| 500% Elongation | 7.08 | 6.62 | 6.49 |
| Tensile Strength at Break (MPa) | 33.77 | 34.90 | 32.20 |
| Force at 300% Elongation (N) | 1.23 | 1.21 | 1.19 |
| Force at 400% Elongation (N) | 1.59 | 1.53 | 1.51 |
| Force at Break (N) | 11.06 | 11.11 | 10.43 |
| Elongation at Break (%) | 690 | 732 | 715 |

"Strength" as used herein can be described as a function of the amount of force necessary to break a sample of prescribed shape and dimensions, such as those used for ASTM test standard D-412. In testing, a glove formed from the nitrile rubber formulation of the present invention with a thickness of about 0.13 mm in the palm area has an unaged average force-at-break reading ranging from 9.23 Newtons (N) to 9.90 N and an aged average force-at-break reading ranging from 10.43 N to 11.11 N. Meanwhile, current market gloves have values ranging from about 6.7 to 14.3 N, with most values between 7.5 and 10.5 N. Thus, the force-at-break for gloves formed from the nitrile rubber formulation of the present invention is similar to that of currently available gloves.

Further, a glove formed from nitrile rubber formation of the present invention has an unaged tensile strength at break ranging from 28.32 MPa to 30.63 MPa and an aged tensile strength at break ranging from 32.20 MPa to 34.90 MPa. Moreover, a glove formed from the nitrile rubber formulation of the present invention has an unaged elongation at break ranging from 715% to 724% and an aged tensile strength at break ranging from 690% to 732%. Additionally, at 300% stretch-elongation, a glove formed from the nitrile rubber formulation of the present invention exhibits an unaged modulus ranging from 3.08 MPa to 3.18 MPa and an aged modulus ranging from 3.69 MPa to 3.81 MPa.

The nitrile rubber formulation of the present invention is useful in manufacturing process for elastomeric articles composed of acrylonitrile materials. The invention affords the ability to produce nitrile rubber articles which closely mimic the physical properties of elastomeric articles made from natural rubber latex. The invention can be advantageously incorporated into the manufacture of a variety of products, such as medical examination or surgical gloves, condoms, probe covers, dental dams, finger cots, catheters, and the like.

The present invention has been described both in general and in detail by way of examples. These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An elastomeric article comprising a compounded nitrile rubber formulation, the compounded nitrile rubber formulation comprising a nitrile rubber, an alkali agent, a metal oxide, a sulfur crosslinking agent, a vulcanization accelerator, and a stretch modifier, wherein the stretch modifier includes particles having a mean particle size ranging from about 0.5 micrometers to about 25 micrometers.

2. The elastomeric article of claim 1, wherein the alkali agent is present in the compounded rubber nitrile formulation in an amount ranging from about 0.1 parts to about 0.99 parts based on 100 dry parts of the nitrile rubber.

3. The elastomeric article of claim 1, wherein the metal oxide is present in the compounded rubber nitrile formulation in an amount ranging from about 0.01 parts to about 0.5 parts based on 100 dry parts of the nitrile rubber.

4. The elastomeric article of claim 1, wherein the combined amount of the alkali agent and the metal oxide present in the compounded rubber nitrile formulation is less than or equal to 1, based on 100 dry parts of the nitrile rubber.

5. The elastomeric article of claim 1, wherein the stretch modifier is a wax emulsion.

6. The elastomeric article of claim 5, wherein the wax emulsion comprises a micronized wax.

7. The elastomeric article of claim 6, wherein the micronized wax includes a polyethylene wax, an oxidized polyethylene wax, a modified polyethylene wax, a high density polyethylene wax, an oxidized high density polyethylene wax, a modified high density polyethylene wax, a polypropylene wax, a polyamide wax, a polytetrafluoroethylene wax, or a combination thereof.

8. The elastomeric article of claim 1, wherein the stretch modifier is present in the compounded rubber nitrile formulation in an amount ranging from about 0.1 parts to about 10 parts, based on 100 dry parts of the nitrile rubber.

9. The elastomeric article of claim 1, wherein the elastomeric article exhibits a tensile strength at break B ranging from about 20 MPa to about 50 MPa.

10. A method of making an elastomeric article, the method comprising: a) preparing a compounded nitrile rubber formulation comprising a nitrile rubber, an alkali agent, a metal oxide, a sulfur crosslinking agent, a vulcanization accelerator, and a stretch modifier, wherein the stretch modifier includes particles having a mean particle size ranging from about 0.5 micrometers to about 25 micrometers; b) dipping a mold into the compounded rubber nitrile formulation; and c) curing said compounded nitrile rubber formulation to form the elastomeric article.

11. The method of claim 10, wherein the alkali agent is present in the compounded rubber nitrile formulation in an amount ranging from about 0.1 arts to about 0.99 arts based on 100 dry parts of the nitrile rubber.

12. The method of claim 10, wherein the metal oxide is present in the compounded rubber nitrile formulation in an amount ranging from about 0.01 parts to about 0.5 parts based on 100 dry parts of the nitrile rubber.

13. The method of claim 10, wherein the combined amount of the alkali agent and the metal oxide present in the compounded rubber nitrile formulation is less than or equal to 1, based on 100 dry parts of the nitrile rubber.

14. The method of claim 10, wherein the stretch modifier is a wax emulsion.

15. The method of claim 14, wherein the wax emulsion comprises a micronized wax.

16. The method of claim 15, wherein the micronized wax includes a polyethylene wax, an oxidized polyethylene wax, a modified polyethylene wax, a high density polyethylene wax, an oxidized high density polyethylene wax, a modified high density polyethylene wax, a polypropylene wax, a polyamide wax, a polytetrafluoroethylene wax, or a combination thereof.

17. The method of claim 10, wherein the stretch modifier is present in the compounded rubber nitrile formulation in an amount ranging from about 0.1 parts to about 10 parts, based on 100 dry parts of the nitrile rubber.

18. The method of claim 10, wherein the nitrile rubber formulation is adjusted to a pH ranging from about 9 to about 11.

* * * * *